United States Patent [19]

Melman

[11] Patent Number: 5,853,767

[45] Date of Patent: *Dec. 29, 1998

[54] COMPOSITIONS FOR TREATING FUNGAL, PARASITIC AND/OR BACTERIAL INFECTIONS, ESPECIALLY INFECTIONS OF ORGANS SUCH AS THE SKIN AND VAGINA

[76] Inventor: Steven A. Melman, 8909 Iverleigh Ct., Potomac, Md. 20854

[*] Notice: The term of this patent shall not extend beyond the expiration date of Pat. No. 5,480,658.

[21] Appl. No.: 778,269

[22] Filed: Jan. 2, 1997

[51] Int. Cl.$^6$ .......................... A61K 33/22; A61K 31/19
[52] U.S. Cl. .............................................. 424/659; 514/557
[58] Field of Search .............................. 514/557; 424/659

[56] References Cited

U.S. PATENT DOCUMENTS

| | | |
|---|---|---|
| 5,158,774 | 10/1992 | Inman . |
| 5,266,329 | 11/1993 | Riley, Jr. . |
| 5,292,532 | 3/1994 | Bombart . |
| 5,451,335 | 9/1995 | Hieatt et al. . |
| 5,480,658 | 1/1996 | Melman ................................. 424/659 |
| 5,489,435 | 2/1996 | Ratcliff . |

OTHER PUBLICATIONS

Label from Oticlean–A Ear Cleaner Manufactured by ARC Laboratories, 1980.
Label from R–7 Ear Cleaner, manufactured by Gimborn U.S.A. 1989.
Bausch & Lomb brand Acetic Acid 2% Aluminum Acetate (Borofair) Manufactured by Pharmafair, Dec. 26, 1991.
Asikoglu et al., *The Release of Isoconazole Nitrate From Different Suppository Bases: In–vitro Dissolution, Physicochemical and Microbiological Studies,* (1995) (Asikoglu–1).
Hart, Boric Acid Vaginal Suppositories, 27 Annals of Pharmacotherapy 1355 (1993) (Hart).
Hart, *Boric Acid Vaginal Suppositories,* 27 Annals of Pharmacotherapy 1355 (1993) (Hart).
Package Insert: Floraouin Vaginal Tablets®, G.D. Searle Ltd., South Africa, 13 Feb. 1975.
Redondo–Lopez et al., *Torulopsis Glabrata Vaginitis: Clinical Aspects and Susceptibility to Antifungal Agents,*, 76(4) Am. J. Obstet. Gynecol. 651 (1990) (Redondo–Lopez).
Van Slyke, Michel & Rein, *Treatment of Vulvoginal Candidiasis with Boric Acid Power,* 141 (2) Am. J. Obstet. Gynecol. 145 (1981) (Van Slyke).

Erkan et al., *Treatment of Otomycosis with Acetic and Boric Acid,* Revista Iberoamericana de Micologia 1993, pp. 33–35.
Michael F. Rein, M.D., *Nystatin vs. Boric Acid Power In Vulvovaginal Candidiasis,* Correspondence, pp. 992–993.
Chapter 9 of Systemic Fungal Diseases, pp. 148–150, Merck Manual of Diagnosis and Therapy (15th Ed.), Merck & Co. Inc. 1989.
Sale of Veterinarial Ear Cleaner at Trade Show on Sep. 20, 1992. Formulation of cleanser sold is same as on batch record dated Nov. 18, 1992.
Biological Abstracts 96:100793 (1993).
Chapter 177, Common Gyneclolgical Problems, *Vaginal Discharge and Inflammation,* pp. 1674–1676, Merck Manual of Diagnosis and Therapy (15th Ed.), Merck & Co. Inc., 1989.
Nyirjesy et al., *Chronic Fungal Vaginitis: The Value of Cultures,* 173(3) (I) Am. J. Obstet. Gynecol. 820 (1995) (Nirjesy).
Label from Oticlean–A Ear Cleaner manufactured by ARC Laboratories, 1980.
Label from R–7 Ear Cleaner, manufactured by Gimborn U.S.A., 1989.
Bausch & Lomb brand Acetic Acid 2% Aluminum Acetate (Borofair) Manufactured by Pharmafair, Dec. 26, 1991.
Jain S.K. et al., Mycoses, vol. 37, pp. 299–301 (1994).
Swate et al., Obstetrics and Gynecology, vol. 43, No. 6, pp. 893–895 (Jun. 1974).

*Primary Examiner*—Marianne M. Cintins
*Assistant Examiner*—M. Moezie
*Attorney, Agent, or Firm*—Jacobson, Price, Holman & Stern, PLLC

[57] ABSTRACT

A method for treating infections, bacterial, fungal and parasitic in origin, especially infections of organs such as the vagina and skin, is provided and involves administering to a patient in need thereof a composition comprising boric acid and acetic acid, in effective amounts. Such a composition is especially useful as a broad based treatment of vaginal infections of unknown bacterial or fungal origin and can be used without the need for medical diagnosis or while such a diagnosis is being determined. Such a composition is effective, safe, providing an alternative to existing forms of treatment which are toxic and is environmentally friendly.

14 Claims, No Drawings

COMPOSITIONS FOR TREATING FUNGAL, PARASITIC AND/OR BACTERIAL INFECTIONS, ESPECIALLY INFECTIONS OF ORGANS SUCH AS THE SKIN AND VAGINA

FIELD OF INVENTION

This invention relates generally to a method for the treatment of infections, bacterial, parasitic or fungal in origin, especially infections of organs such as the vagina and skin. This invention further relates to a composition in a form suitable for treating vaginal infections and skin conditions.

BACKGROUND OF THE INVENTION

Vaginitis is a frequent cause of distress and discomfort in adult women accounting for about 10 million physician office visits per year in the U.S. The three major causes of this inflammation and the corresponding symptoms of abnormal discharge, itching, burning, dyspareunia and dysuria, include vaginal candidiasis, bacterial vaginosis and trichomonas.

Traditionally the treatment for vaginal and ear candidiasis has been the imidazole/triazole related antifungal compounds. These compounds are primarily effective against *Candida albicans* and provide little to no relief from *Torulopsis glabrata* and *Candida tropicalis*. While terconazole is effective against non-albicans yeast as well as albicans, its use is limited to infections caused by the genus Candida, for example, vulvovaginitis. The recent introduction of over the counter imidazole/triazole compounds such as miconazole, clotrimizole and butconazole is therefore problematic. These compounds are limited in their application being only efficacious against particular types of infection, for example, infection caused by the genus Candida, as in vaginal candidiasis. Without proper testing it is not possible for a patient to know whether they suffer from, for example, vaginal candidiasis or bacterial vaginosis, the symptoms being similar. In other words, what the nature and origin of the infection is.

Additional active ingredients used in the treatment of vaginal candidiasis include sulfanilamide and nystatin. These compounds again are only effective against the genus Candida and prior to their use the diagnosis of vaginal candidiasis should be confirmed by laboratory analysis, such as, cytology including KOH smears, giemsa, Wrights and other stains and/or cultures and/or biopsy. Such diagnosis can mean that proper treatment is delayed.

Common treatments for bacterial vaginosis include oral metronidazole and clindamycin vaginal cream or oral. Metronidazole taken orally causes gastro-intestinal distress, creates a metallic taste for the course of treatment and has been shown to be carcinogenic in mice and rats. Clindamycin therapy has been associated with severe colitis which may end fatally. Additionally, while these compositions are effective in eliminating the bacterial vaginosis, their use may cause yeast propagation and resulting vaginal candidiasis.

Trichomonas and related parasites are treated with antibiotics such as metronidazole.

There is currently no product available, either over the counter or by prescription, that may be used to safely and effectively treat, for example, vaginal infections of both bacterial and fungal origin. It would therefore be extremely advantageous to provide such a product that can be used for the treatment of vaginal infection such as symptomatic vaginal discharge, vaginitis and the like in which the cause, based on the symptoms alone, may be indeterminable without specific medical diagnosis, and may be either bacterial or fungal in nature. Furthermore to provide a product which may be used as an interim treatment while actual diagnosis is being determined and/or as an alternative to existing treatment products which may be toxic and environmentally unfriendly.

Acetic acid is known to have antimicrobial capacities and is effective at various percentages against Pseudomonas, Staphylococcus, Streptococcus and various yeasts. The fungitoxic effects of acetic acid on fungi causing otomycosis has been examined in *Mycoses* 37: 299–301 (1994). In this study various volatile compounds, including acetic acid, were tested, in vitro, for their fungitoxic effects against five fungi. Some antifungal effect was illustrated for acetic acid. *Candida albicans* was shown to be the most resistant to the volatiles. Boric acid is known to be an effective antibacterial and antifungal agent and has been prepared in the form of a suppository for the treatment of fungal infection alone (see *The Annals of Pharmacotherapy* 1993, Volume 27, pp.1355–1357). Boric acid has been shown to be fungistatic against *Candida albicans* wherein in vitro tests show that it is effective in treating vulvovaginal candidiasis (see *Obstet. Gynecol.*, (1974) 43:893–895, "Boric Acid Treatment of Vulvovaginitis").

Acetic acid and boric acid have been used separately in vivo for the treatment of otomycosis (see *Revista Iberoamericana de Micologia* (1993) :10: pp. 33–35). In this study two groups of patients were tested. Group A patients were treated with a combination of acetic acid (2%), hydrocortisone (1%) and sterile water (to 100%). Group B patients were treated with boric acid (4%) saturated in absolute alcohol (25%) and sterile water (to 100%). A composition comprising both acetic acid and boric acid was not used.

A solution comprising, as active ingredients, both acetic acid and boric acid is disclosed in my U.S. Pat. No. 5,480,658, the disclosure of which is expressly incorporated herein by reference. The composition as described in this patent is useful in cleaning the ears of pets.

SUMMARY OF THE INVENTION

A composition comprising acetic acid and boric acid, in particular amounts, has now surprisingly been found to be effective in the broad based treatment of bacterial and fungal infection in skin, i.e., the composition has been found to have bacteriostatic, bacteriocidal and anti-fungal properties. It is envisioned that the composition according to the present invention will therefore provide effective broad treatment of vaginal infections, such as vaginitis.

Such a composition has also been found to be useful in the treatment of various skin conditions (including hairy regions of the skin, such as, the scalp, body and pubic regions) related to bacterial, fungal or parasitic infection. Such skin conditions may be fungal in origin, for example, dermatocandidiasis caused by *candidiasis albicans*. Other examples of skin conditions in which the composition of the present invention is deemed useful include fungal infections from the genera Trichophyton, Epidernophyton and Microsporum, such as *Tinea pedis* (athletes foot), *Tinea cruris* (jock itch), and *Tinea capitis*. Other conditions include infections from *Sarcoptes scabies*, pediculosis, keratinization disorders, which may be caused by various dermatophytes, and conditions caused by various types of ectoparasites. In other words, the present invention may also be used to treat skin conditions associated with bacterial, fungal and parasitic infections and is antimicrobial, bacteriostatic, bacteriocidal, anti-fungal, keratolytic and keratoplastic.

The composition of the present invention enables treatment of vaginal and skin infections of unknown origin without the need for medical diagnosis and/or as an interim treatment during medical diagnosis. It is envisioned that the composition would be advantageously used as an interim form of treatment of vaginal infections by medical practitioners and would also provide the public with a safe, effective and environmentally friendly alternative to existing products.

A particular advantage in combining acetic acid with boric acid is that the pH of the composition may be readily adjusted to allow therapeutic amounts of each component while maintaining the pH at a level that is most effective for the treatment of organs such as the vagina and skin.

Therefore, in accordance with one embodiment of the present invention, a method for the treatment of vaginal infection of bacterial or fungal origin, including vaginitis, symptomatic vaginal discharge and bacterial or fungal vaginosis, is provided comprising administering to a patient in need thereof an effective amount of a composition which comprises both acetic acid and boric acid, and a pharmaceutically acceptable carrier.

Such a composition is most preferably administered in the form of a suppository although other dosage forms are also advantageously envisioned. Advantages to administering the composition as a suppository include convenience, ease of application, increased safety and neatness. Other dosage forms include solutions, for douching and the like, creams, ointments, gels, creme rinses and foams.

Administering the composition as a cream having a low surface tension is advantageous as it provides a uniform wetting action that assists in composition penetration into vaginal crypts and crevices.

Providing the composition in the form of a solution, which may initially be provided in a concentrated liquid form, or as a dissolvable powder, tablet or the like requiring the addition of water prior to use, enables the composition to be administered as a vaginal douche. As a vaginal douche, the composition can also be used in a prophylactic manner and for hygiene purposes.

In accordance with another embodiment of the present invention, the composition may be used for treating skin conditions, particularly skin conditions associated with bacterial, fungal or parasitic infection, comprising topically applying to affected areas of the skin an effective amount of a composition according to the present invention. Such a composition is preferably in a form most suitable for topical application and includes creams, ointments, gels, shampoos, creme rinses, foams and solutions, including cleansing solutions.

PREFERRED EMBODIMENTS OF THE PRESENT INVENTION

The present invention is directed to a method for treating various bacterial and/or fungal infections, particularly vaginal infections and skin conditions, with compositions of acetic acid and boric acid. Such a composition enables broad treatment of either bacterial or fungal infection and may be used without the need to determine the nature of the infection by precise medical examination, as a safe and effective alternative to existing products or as an interim form of treatment during medical diagnosis. The composition is particularly useful in the treatment of vaginal infections the symptoms of which may be similar for bacterial and fungal infections and the origin of which may only be determinable by precise medical examination. Examples of symptoms which may be present in either fungal or bacterial vaginal infections include symptomatic vaginal discharge, vaginitis and vaginosis.

As mentioned above, acetic acid has antimicrobial capacities and is effective at various percentages against Pseudomonas, Staphylococcus, Streptococcus and various yeasts. Boric acid is an effective antibacterial and antifungal agent. Both acetic acid and boric acid act as acidifying agents.

The composition of the present invention comprises both acetic acid and boric acid and is both anti-fungal and anti-bacterial. The composition is active, independent of pH, in the presence of blood, pus or vaginal secretions.

The composition of the present invention is in any form suitable for treatment of the vagina and skin, such as, for example, solutions, gels, shampoos, creams, creme rinses, ointments, suppositories, tablets and powders. The amount of acetic acid and boric acid in the composition is an amount which is safe and effective and varies depending on the nature of the composition, the organ and animal being treated and the severity of the infection. Such an amount is determinable by a person of skill in the art. Acetic acid preferably comprises about 0.1% to 10.0% by weight of the composition, more preferably 2.0–5.0% by weight of the composition. Boric acid preferably comprises about 0.1% to 30.0% by weight of the composition, more preferably about 2.0–12.0% by weight of the composition.

Where the composition is applied as a suppository, the active ingredients are combined with inert suppository bases, depending on the nature of the suppository, such as cocoa butter, glycerinated gelatin, hydrogenated vegetables oils, mixtures of polyethylene glycols of various molecular weights and fatty acid esters of polyethylene glycol. Means of creating these suppository bases are known to those skilled in the art. The use of soluble or dispersible bases such as polyethylene glycols or glycol surfactant combinations has the substantial advantage of lack of dependence on melting point approximating body temperature. Moreover, handling, storage and shipping are considerably simplified.

The preparation of such suppository compositions includes well known techniques of rolling (hand shaping), molding (fusion) and cold compression. Suppositories are usually globular or oviform and weigh about 5 gram. Reference is made to *Remington's Pharmaceutical Sciences*, 18th Edition, Chapter 87, pages 1609–13 (1990), the disclosure of which is expressly incorporated herein by reference.

The composition may include a water soluble base. A water soluble base lowers the surface tension of the composition aiding in a more thorough distribution of the composition. A water soluble base also decreases the risk of secondary infection. Illustrative water soluble bases are corn starch, aloe, cocoa butter and the like.

The compositions of the invention may include propylene glycol. Propylene glycol acts as a surfactant and assists in penetration, contact, and absorption of the active ingredients. Propylene glycol also serves as a preservative.

The compositions of the invention may also include a non-ionic surfactant, such as polysorbate. Such a surfactant provides better surface contact of the composition with the vaginal mucosa by further reducing surface tension.

The compositions of the invention may also be used as a carrier material for and/or in combination with other medicines, such as antibiotics, spermicidal agents, anti-inflammatories, thereby further broadening the compositions medical efficacy. It is envisioned that the composition may be combined with for example antibiotics so as to extend the scope of treatment to other types of vaginal infections currently not treatable by the combination of acetic and boric acid alone.

The composition of the present invention may also be pH balanced by the addition of a base, such as triethanolamine, to adjust the pH to a level compatible with the organ being treated. In the normal vagina, the pH is between approximately 3.8–4.4. In normal skin the pH is between approximately 5.6–6.6. In order to prevent irritation of the skin or vagina from a composition that is too acidic, the pH is adjusted to a point where the irritation is minimal or nonexistent, while still being effective against microorganisms, including yeast. As mentioned above, using acetic acid in combination with boric acid makes it possible to more effectively adjust the pH of the composition such that the vaginal areas can be safely and effectively treated.

A humectant may also be included in the composition of the present invention, such as glycerin, to soothe the area being treated, for example, in cleansing solution compositions.

The composition of the present invention may also include a topical anesthetic such as lidocaine hydrochloride and topical steroids, such as corticosteroid, to provide relief from pain or itching during treatment.

As will be understood by those skilled in the art, the regimen for treating vaginal infection and/or skin conditions will depend on the severity of the infection and the form of the composition. By way of example, where the composition is in the form of a cream, the cream is topically applied to the affected area. Where the composition is in the form of a suppository, the suppository is inserted into the vagina, most preferably twice daily for 7 days.

Terms used herein are to be given their usual meaning in the art unless otherwise stated. The term "vaginal infection" means any vaginal infection of bacterial or fungal origin. Examples of some of the microorganisms which cause such infections include microorganisms of the genus Candida, particularly *C. albicans* and *C. tropicalis* and *T. glabrata*, gardneralla vaginalis, various mixed anaerobic bacteria and *peptostreptococcus* bacteria.

The term "skin condition" means any skin condition which results from bacterial, parasitic, fungal infection and keratinization disorder. Examples of microorganisms which can cause such infections include *candidiasis albicans*, microorganisms of the genera Trichophyton, Epidermophyton and Microsporum, bacteria such as *Sarcoptes scabies*, and other various dermatophytes, and various types of ectoparasites.

The term "effective amount" is an amount which is effective in treating a particular infection and is determinable by a person of skill in the art.

Preparation of each of the formulations described herein would be within the ambit of the person of skill in the art, although reference is made to *Remington's Pharmaceutical Sciences,* 18th Edition (1990), the disclosure of which is expressly incorporated herein by reference.

The present invention will now be described by way of reference to the following examples which are not to be construed in such a manner as to limit the scope of the present invention.

EXAMPLE 1—VAGINAL SUPPOSITORY

A suitable formulation for a composition in the form of a suppository for treating vaginal infection is given as follows:

600 mg boric acid (powder)
0.1–10% by weight (glacial) acetic acid
cocoa butter

PREPARATION

The suppository essentially comprising the above formulation can be prepared as mentioned above in accordance with well known techniques in the art. The amount of cocoa butter may vary but will be sufficient to compound the suppository.

APPLICATION

Treatment of the vaginal infection may very depending on the severity of the infection. In general, a suitable treatment regime would be to insert the suppository into the vagina, twice daily for 7 days.

EXAMPLE 2—VAGINAL SOLUTION

A suitable formulation for a solution according to the present invention for the treatment of vaginal infection is given as follows, wherein the percentages are given as %w/w of the total composition:

0.1–0.5% boric acid
2% (glacial) acetic acid
water

For a douche solution other ingredients may be added and include those typically found in vaginal douches such as other antimicrobial agents, anaesthetics or antipruitics (such as phenol or menthol), astringents and surface active agents. The solution may be initially formed as a concentrated liquid, dissolvable powder or tablet. When use is desired, water may be added, preferably warm in temperature, to produce a solution of desired concentration.

Other ingredients such as propylene glycol, glycerin USP and Polysorbate 20 (Liposorb L20) may be added.

EXAMPLE 3—SKIN TREATMENT AND CLEANSING SOLUTION

A suitable formulation for a composition in the form of a solution for treatment of skin infection and cleansing is given as follows, in which the percentages are given as %w/w of the total composition:

81% water
2% boric acid powder
2% glacial acetic acid
5% propylene glycol
5% glycerin USP
5% Polysorbate 20 (Liposorb L20)

PREPARATION

The solution is prepared by adding water to a suitable tank. The remaining ingredients are mixed in slowly until completely dissolved. The mixed solution is uniform and clear. The solution may be further diluted by the addition of water.

APPLICATION

The solution can be applied to the infected area of the skin by any suitable means such as cotton wool, cotton swab or the like.

EXAMPLE 4—SHAMPOO

A suitable formulation for a composition in the form of a shampoo according to the present invention is given as follows, in which the percentages are given as %w/w of the total composition:

- Water 59.3–66.1%
- Methocel F4m 0.2–0.3%
- Glucamate DOE 120 1.0–1.5%
- Alpha Olefin Sulfonate (40%) 20–23%
- Lauramide DEA 0.8–1%
- Boric Acid (powder) 2%
- Acetic Acid (glacial—99) 2%
- Cocamidopropyl Betaine 6–8%
- Coconut (fragrance) 0.27%
- Glycerin USP 0.5%
- Safflower Oil 0.003%
- Kathon CG 0.1%
- Sodium Lactate 1–2%

PREPARATION

Add to a suitable mixing tank, water as above. Add the Methocel F4M and Glucamate DOE 120 slowly. Mix until uniform and completely free of lumps. Continue to add and mix in the remaining ingredients until uniform.

APPLICATION

The shampoo can be used by massaging a suitable amount, such as about 5 mls, of the shampoo into the hair and/or body and rinsing off with warm water. The shampoo is suitable for use on all hairy regions of the body including scalp and pubic areas, as often as deemed necessary.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A composition comprising acetic acid in an amount between 0.1–10% by weight of the total composition and boric acid in an amount between 0.1–30% by weight of the total composition; wherein said composition is in a form suitable for vaginal treatment being selected from the group consisting of vaginal suppository, vaginal douche, vaginal shampoo, vaginal cream, vaginal ointment; vaginal gel, vaginal creme rinse, vaginal foam and vaginal solution.

2. The composition of claim 1 wherein the composition is in the form of a vaginal suppository.

3. The composition of claim 1 wherein the composition is in the form of a vaginal douche.

4. The composition of claim 1 further comprising a surfactant.

5. The composition of claim 4 wherein the surfactant is propylene glycol.

6. The composition of claim 1 further comprising a non-ionic surfactant.

7. The composition of claim 6 wherein the non-ionic surfactant is polysorbate.

8. The composition of claim 1 further comprising a pH adjuster.

9. The composition of claim 8 wherein the pH adjuster is triethanolamine.

10. A composition in the form of a vaginal suppository comprising 600 mg boric acid, 0.1–10% by weight glacial acetic acid, wherein said percentages are by weight of the total composition.

11. The composition of claim 10 further comprising an inert base.

12. The composition of claim 11 wherein said inert base is selected from the group consisting of cocoa butter, glycerinated gelatin, hydrogenated vegetable oil, polyethylene glycols and fatty acid esters of polyethylene glycols.

13. A composition in the form of a vaginal douche consisting essentially of 0.1–0.5% boric acid and 2% glacial acetic acid, wherein said percentages are by weight of the total composition.

14. The composition of claim 12 further comprising of water.

* * * * *